United States Patent [19]
Greengrass et al.

[11] Patent Number: 5,976,110
[45] Date of Patent: Nov. 2, 1999

[54] CATHETER SYSTEM FOR ADMINISTRATION OF CONTINUOUS PERIPHERAL NERVE ANESTHETIC

[75] Inventors: Roy A. Greengrass, Chapel Hill; Susan M. Steele; David H. Gleason, both of Durham, all of N.C.

[73] Assignee: Duke University, Durham, N.C.

[21] Appl. No.: 09/006,643

[22] Filed: Jan. 14, 1998

[51] Int. Cl.[6] .................................................. A61M 5/178
[52] U.S. Cl. .......................... 604/158; 604/272; 604/506; 604/508; 604/512
[58] Field of Search .............................. 604/158, 20, 21, 604/159, 272, 273, 500, 503, 506, 508, 512, 513; 601/15; 606/32, 41; 607/1, 2, 3, 46, 47, 63, 115

[56] References Cited

U.S. PATENT DOCUMENTS

| | | | |
|---|---|---|---|
| 4,518,383 | 5/1985 | Evans | 604/51 |
| 4,775,367 | 10/1988 | Schmidt | 604/192 |
| 4,889,529 | 12/1989 | Haindl | 604/274 |
| 4,917,668 | 4/1990 | Haindl | 604/167 |
| 4,917,670 | 4/1990 | Hurley et al. | 604/51 |
| 4,994,036 | 2/1991 | Biscoping et al. | 604/158 |
| 5,085,631 | 2/1992 | Leighton | 604/28 |
| 5,106,376 | 4/1992 | Mononen et al. | 604/164 |
| 5,119,832 | 6/1992 | Xavier | 128/786 |
| 5,135,525 | 8/1992 | Biscoping et al. | 604/51 |
| 5,312,374 | 5/1994 | Gurmarnik | 604/264 |
| 5,328,479 | 7/1994 | Gurmarnik | 604/158 |
| 5,378,241 | 1/1995 | Haindl | 604/164 |
| 5,512,052 | 4/1996 | Jesch | 604/158 |
| 5,630,802 | 5/1997 | Moellmann et al. | 604/164 |

*Primary Examiner*—Wynn Wood Coggins
*Assistant Examiner*—N. Kent Gring
*Attorney, Agent, or Firm*—Jenkins & Wilson, P.A.

[57] ABSTRACT

A catheter system having an epidural needle, an electrically conductive stimulation wire attached to the needle, a multi-purpose connector, which is adapted to connect to intravenous tubing for supplying local anesthesia, and an epidural catheter for supplying regional anesthesia. When the connector and needle are connected to each other, an operator can insert the needle into a patient with the needle's distal end within the nerve sheath and proximate to the nerve plexus. A voltage is applied via the wire to determine correct positioning. Then, the operator can slide the catheter through the connector and needle until the catheter's distal end is protruding out of the needle's distal end and into the nerve sheath, proximate to the nerve plexus. Then, the needle (and its associated wire) and the connector (and its associated tubing) are slidably removed from the catheter, and the catheter may be left in place.

14 Claims, 5 Drawing Sheets

CATHETER SYSTEM FOR ADMINISTRATION OF CONTINUOUS PERIPHERAL NERVE ANESTHETIC

TECHNICAL FIELD

The present invention relates generally to catheters for administration of local anesthesia to achieve peripheral nerve blockade, such as is useful when a surgeon operates on a patient's arm or leg. More particularly, the present invention relates to an improved catheter system that includes an epidural needle with a TUOHY-type beveled aperture (commonly known as a TUOHY needle) and with an attached stimulation wire, an epidural catheter, and a multi-purpose connector adapted to connect to a tube (such as an intravenous tube) and adapted to receive (such as via a hemostatic valve) the epidural catheter.

BACKGROUND OF THE INVENTION

As employed herein, the terms "local" and "regional" with respect to anesthesia are intended to be synonymous and interchangeable.

When a surgeon operates on the legs or arms, local anesthesia may be performed as continuous regional anesthesia. In continuous regional anesthesia, by using an epidural needle, a catheter is then introduced through the needle, with the front, distal end of the catheter projecting out of the needle to lie beside the nerves. Typically, in order to determine correct positioning of the needle, a small, test dose of anesthesia is administered through the needle, followed by inserting the catheter through the needle. Selected catheters have an integral conductive wire through which an electrical current may be applied to determine correct positioning after the catheter has been inserted through the needle. Then, the needle is removed and the catheter is left in place so that more local anesthetic drugs can be administered through the catheter.

Various attempts have been made to improve on anesthesia instruments.

For instance, U.S. Pat. No. 5,119,832 to Xavier shows an epidural catheter that includes four (4) circumferential ring electrodes, each connected to conductive wires embedded in the wall of the catheter. Thus, anesthetics or narcotics can be administered through the catheter, in conjunction with providing electrical stimulation through the electrodes in order to control pain.

Additionally, of interest is U.S. Pat. No. 5,378,241 to Haindl, which shows an epidural cannula with a TUOHY-type beveled aperture such that the cannula has a sufficiently large diameter so that both an epidural catheter and a spinal cannula can be simultaneously positioned inside of the epidural cannula.

In another variation, a guide wire is first inserted through a spinal cannula that is inside of an epidural cannula, followed by removing the spinal cannula and then inserting a spinal catheter over the path of the guide wire and within the epidural cannula, as disclosed in U.S. Pat. No. 4,994,036 to Biscoping et al.

Various other anesthesia instruments of interest are disclosed in U.S. Pat. No. 4,518,383 to Evans; U.S. Pat. No. 4,775,367 to Schmidt; U.S. Pat. No. 4,889,529 to Haindl; U.S. Pat. No. 4,917,670 to Hurley et al.; U.S. Pat. No. 4,917,668 to Haindl; U.S. Pat. No. 5,085,631 to Leighton; U.S. Pat. No. 5,106,376 to Mononen et al.; U.S. Pat. No. 5,135,525 to Biscoping et al.; U.S. Pat. No. 5,312,374 to Gurmarnik; U.S. Pat. No. 5,328,479 to Gurmarnik; U.S. Pat. No. 5,512,052 to Jesch; and U.S. Pat. No. 5,630,802 to Moellmann et al.

The disclosures of all patents mentioned are incorporated herein by reference.

SUMMARY AND OBJECTS OF THE INVENTION

In accordance with the present invention, provided is a catheter system comprising: (a) an epidural needle, (b) an attached electrically conductive stimulation wire, (c) a multi-purpose connector, and (d) an epidural catheter.

The epidural needle has a distal end and a proximal end, with the distal end terminating in a beveled aperture and having a sharp tip adapted for insertion into a nerve sheath (alongside a nerve plexus) of a patient, and with the proximal end being adapted for connection, such as to the below-described multi-purpose connector.

The electrically conductive stimulation wire is connected at one end of the wire to the epidural needle in a manner that allows for conduction of an electrical voltage along the stimulation wire to the distal end of the epidural needle and is at another end of the wire adapted for connection to a nerve stimulator device.

The multi-purpose connector has a distal end, a proximal end, and an aperture in the middle. The distal end is adapted for fluid connection to the epidural needle's proximal end. The proximal end is adapted to close the multi-purpose connector and also is adapted to receive an epidural catheter (such as the below-described epidural catheter). The middle aperture is adapted for fluid connection to flexible tubing, such as an intravenous tube, for administration of a solution, such as a local anesthetic. The multi-purpose connector may suitably be an adapter with its proximal end defining a hemostatic valve, as described in detail below.

The epidural catheter is adapted for insertion within and through the multi-purpose connector and within and through the epidural needle with the catheter's distal end protruding out of the needle's distal end, and also is adapted for continuous administration of regional anesthesia.

It is therefore an object of the present invention to provide a catheter system including components, such that when they are attached to each other, the system allows for one person to operate it in order to locate precise positioning of an epidural needle by electrically stimulating and thus locating nerve(s), to aspirate, preferably simultaneously, for blood to determine if inadvertently a blood vessel has been punctured, and also to inject local anesthesia via the needle prior to insertion of an epidural catheter, as well as to insert an epidural catheter through the needle for continuous administration of regional anesthesia.

Some of the objects of the invention having been stated above, other objects will become evident as the description proceeds below, when taken in connection with the accompanying drawings as best described below.

DETAILED DESCRIPTION OF THE INVENTION

Figure 1:
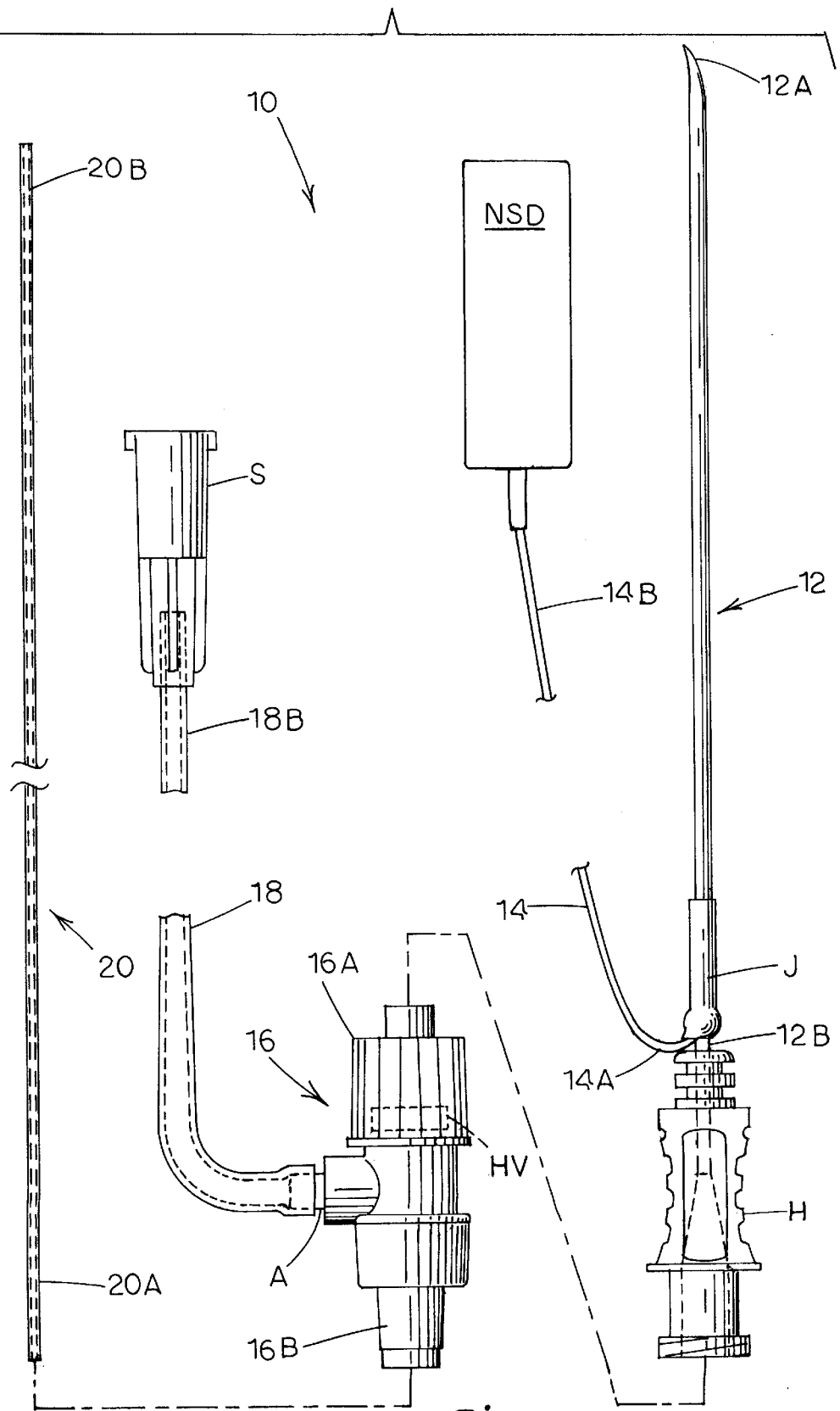
FIG. 1 is a plan view of the disassembled components of the catheter system of the present invention, namely the epidural needle (with the stimulation wire connected to the needle), the multi-purpose connector (with associated intravenous tubing shown attached to the middle aperture of the multi-purpose connector), and the epidural catheter.

FIG. 1 depicts the constituent components of the inventive catheter system, generally designated 10, and FIGS. 2 to 5 depict the procedure for using catheter system 10. The same numerals and letters are employed for the same components depicted in the different Figures.

More particularly, shown is epidural needle 12, having distal end 12A that terminates in a beveled aperture. Epidural needle 12 may suitably be a TUOHY needle in which distal end 12A is bent, opening toward one side. Typically, distal end 12A is a steel impregnated, non-insulated HUBER tip. The remainder of the TUOHY needle is straight, and preferably is substantially covered with insulation, such as an insulative, plastic, heat-shrunk overwrap along and over the length of the needle (distal end 12A should be free of insulation), and terminates in proximal end 12B, illustrated as including fluid attachment to a rigid, plastic epidural needle connector, which is depicted as hub H. Although hub H is illustrated as a standard TUOHY hub that is an integral part of a standard TUOHY needle, applicants contemplate that hub H may be a physically separate part which is attachable to epidural needle 12.

More particularly, for practicing the invention, a suitable epidural needle 12 may be an 18 gauge, steel TUOHY needle with a HUBER tip and a TUOHY hub. Such TUOHY needles are commercially available, with a non-insulated tip and a plastic hub as respective integral portions of the needle. Such TUOHY needles are available in lengths of 2, 4, and 6 inches (5.1, 10.2, or 15.2 cm). The non-winged needle variety preferably should be used.

Also, jacket J is located over a part of the lowermost proximal portion of epidural needle 12, preferably at the juncture of proximal end 12B and hub H. Prior to placement of jacket J on epidural needle 12, a portion of the insulative, plastic, shrink-wrap is removed from epidural needle 12, and electrically conductive stimulation wire 14 is attached by securing its distal end 14A to the exposed area of the conductive needle, followed by placing jacket J there over in order to attach stimulation wire 14 securely to epidural needle 12.

The plastic shrink-wrap is employed so that when an electrical current is supplied to stimulation wire 14, the electrical current does not transfer to the patient other than at distal needle tip 12A. However, applicants contemplate that various other means may be employed to prevent electrical current from transferring to the patient other than transferring at distal needle tip 12A, and it is not intended to limit the invention in connection with the shrink-wrap.

Alternatively for instance, applicants contemplate that the exterior of the TUOHY needle can be painted or coated with an insulating material leaving the extreme tip of the needle exposed. Also, there will be a 5 mm long paint-free area of the needle proximate to the hub for attachment to stimulation wire 14. (Not illustrated.) By minimizing the non-insulated surface area at the tip even more, a more focused current field is possible. This should increase accuracy and performance. This coating process also renders the needle surface smooth and avoids the "step-up" in outer needle diameter resulting from the insulative plastic, heat-shrunk overwrap.

Also, it is contemplated that epidural needle 12 may be manufactured with an insulated wire 14 embedded in needle 12, whereby needle 12 is not insulated. (Not illustrated.)

Proximal end 14B of stimulation wire 14 is illustrated as being attached during use to nerve stimulator device NSD, a suitable commercially available device being the STIM 2000, namely the STIMIPLEX Digital Peripheral Nerve Stimulator available from B. Braun Medical, Inc. Stimulation wire 14 may be any conductive wire that is compatible with the STIM 2000. Typically, a suitable wire length is 20 inches (50.8 cm).

Then, after placement of the TUOHY needle in the patient, a pulse voltage is supplied from nerve stimulator device NSD through stimulation wire 14 and through epidural needle 12 to distal end 12A in order to help determine that distal end 12A is correctly positioned in the patient's peripheral nerve sheath NS beside the patient's nerve plexus NP (see FIGS. 2–5), i.e., a brachial nerve plexus near bicep B of the arm, a sciatic nerve plexus in the leg, a lumbar nerve plexus in the back, etc. As shown in the Figures, artery AR and vein VE may also be present inside nerve sheath NS, like nerve plexus NP is.

Applicants presently use a separate stimulation lead wire with an alligator clip at the proximal end to conduct current from the peripheral nerve stimulator device to the TUOHY needle. However, applicants contemplate that the stimulation lead wire can be integrated into the hub of the TUOHY needle during the molding process, or securely attached, in ways additional to that described above, to the needle close to the hub. With either construction, the objective is to make the catheter system as self-contained as possible so that the user opens the packaging, attaches the wire extending from the needle to the nerve stimulator device and performs the anesthetic nerve block without requiring the introduction of extra cables or attachments in the procedural environment.

Figure 2:
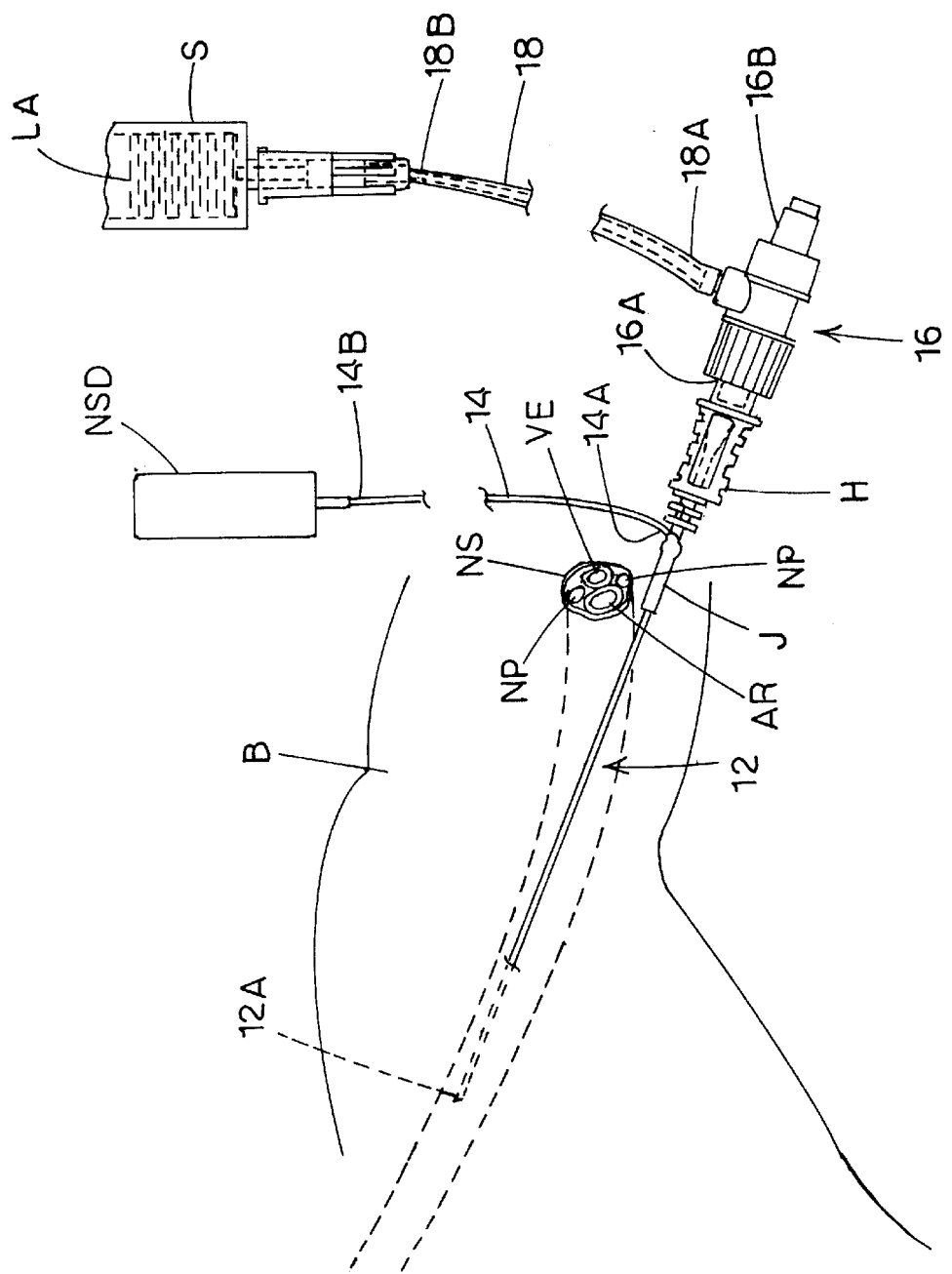
FIG. 2 is a side view of the catheter system of the invention with the epidural needle inserted into the nerve sheath, but without the epidural catheter.
Figure 3:
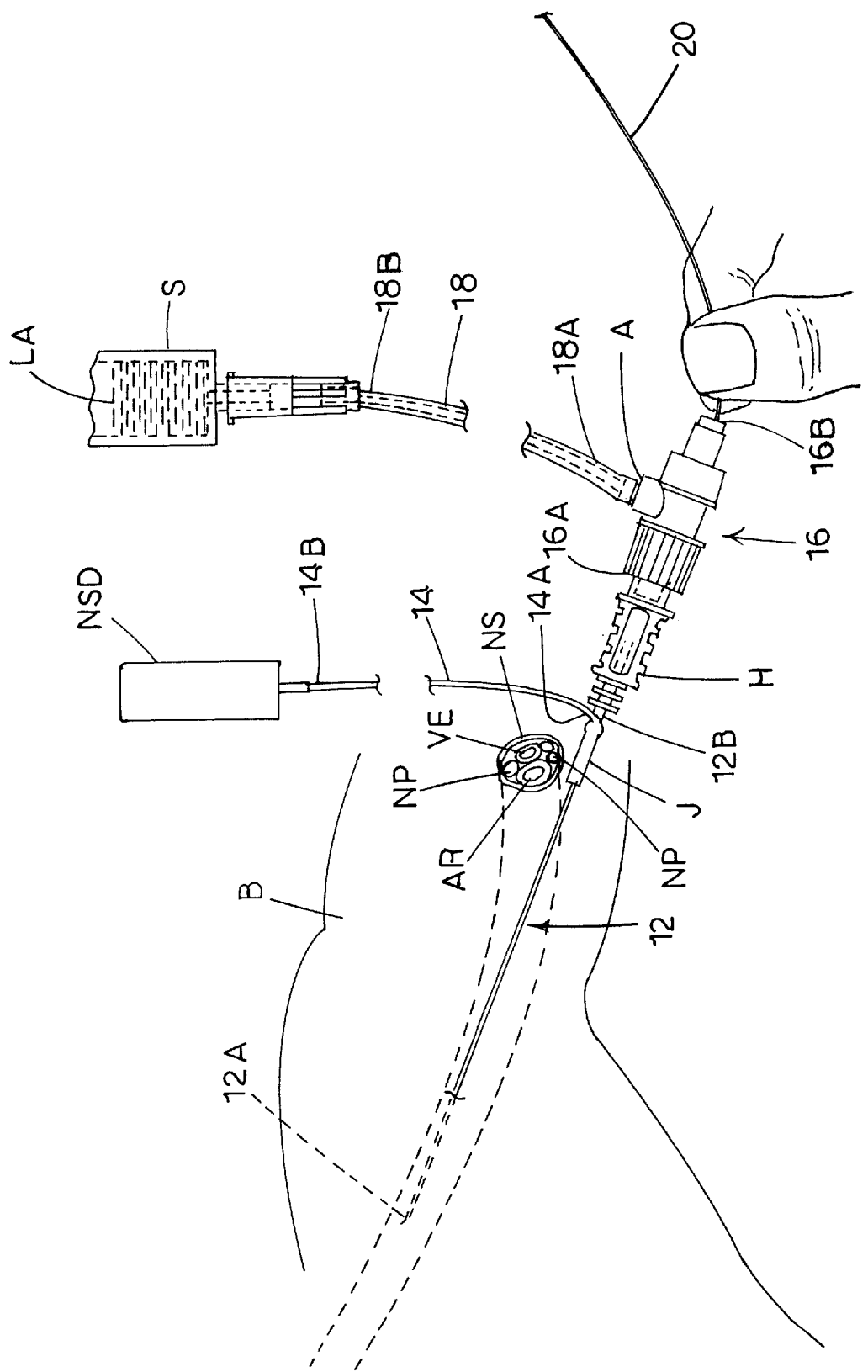
FIG. 3 is a view similar to FIG. 2, in which a person's hand is shown inserting the epidural catheter into the multi-purpose connector of the catheter system.
Figure 4:
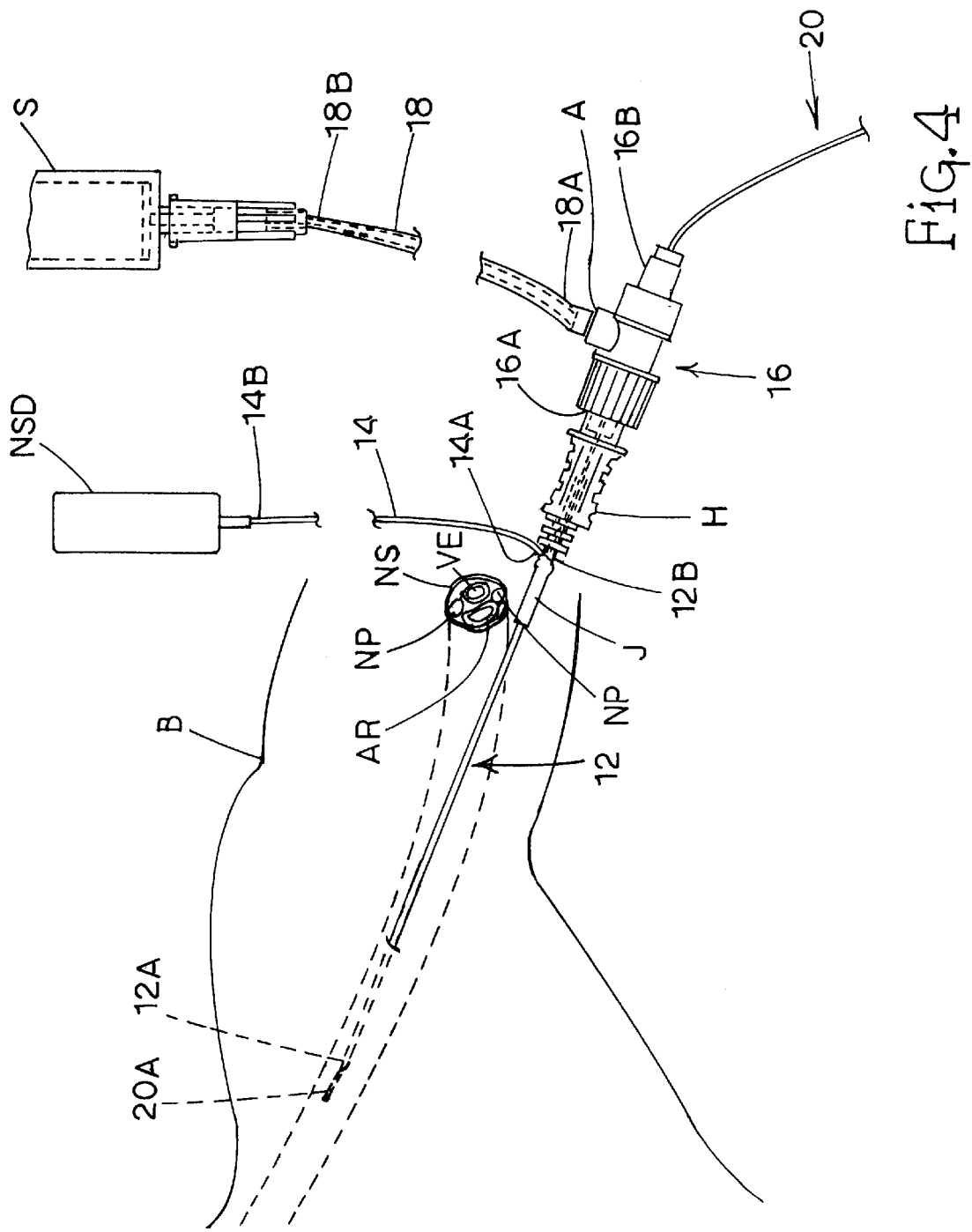
FIG. 4 is a view similar to FIG. 3, but further showing the epidural catheter having been inserted through the multi-purpose connector and the epidural needle, and out the distal end of the needle, with the distal end of the catheter extending into the nerve sheath alongside the nerve plexus.

Multi-purpose connector 16 has distal end 16A, proximal end 16B, and middle aperture A. Multi-purpose connector 16 is shown in its preferred embodiment as an adapter that fluidly connects at its distal end 16A to hub H, as shown in FIGS. 2 to 4.

Middle aperture A of multi-purpose connector 16 is adapted for connecting fluidly to flexible tubing 18 (which may be conventional intravenous tubing) at its distal end 18A. For instance, aperture A may suitably be a side port of the adapter.

Also, tubing 18 is shown fluidly connected at its proximal end 18B to syringe S for administration of a solution, for instance, a dilating agent, such as a saline solution, a local anesthetic solution, or a neurolytic solution. The solution is illustrated in a preferred embodiment as a solution of local anesthesia LA (which may also be employed for dilation, i.e., to create a skin wheal, as described below).

Thus, when multi-purpose connector 16 and epidural needle 12 are assembled and epidural needle 12 of the assembly has been inserted into a patient, then local anesthesia LA may be supplied through tubing 18. Hence, local anesthesia LA will pass out of distal end 18A, through multi-purpose connector 16, into hub H and through epidural needle 12, and out of needle distal end 12A through nerve sheath NS beside nerve plexus NP of the patient.

Proximal end 16B of multi-purpose connector 16 is adapted to receive epidural catheter 20 and distal end 16A preferably includes hemostatic valve HV. Also, proximal end 16B is adapted to selectively close multi-purpose connector 16 to prevent leakage of fluid out of multi-purpose connector 16.

Epidural catheter 20 is adapted for insertion into proximal end 16B of multi-purpose connector 16 so that epidural catheter 20 may be slidably inserted through hemostatic valve HV, and into and through multi-purpose connector 16 and epidural needle 12 when the two are assembled and epidural needle 12 portion of the assembly has been inserted into a patient, resulting in distal end 20A of epidural catheter 20 being located in nerve sheath NS next to nerve plexus NP of the patient. Distal end 20A suitably has a terminal co-axial opening with rounded edges. Opposite proximal end 20B may be provided with a connector for fluidly connecting a syringe to supply regional anesthesia.

A preferred method of using inventive catheter system 10 is as follows.

With reference now to FIG. 2, multi-purpose connector 16 is fluidly attached at its middle aperture A to distal end 18A of tubing 18. Tubing 18 is, in turn, fluidly attached at its proximal end 18B to syringe S, for attachment, if desired, to a supply of a solution, such as local anesthesia LA.

At distal end 16A, multi-purpose connector 16 is then fluidly connected to hub H of epidural needle 12. As described above, epidural needle 12 has already been modified by removing a portion of the insulative plastic and attaching stimulation wire 14 to the area and covering the area with jacket J to hold wire 14 in place. Proximal end 14B of stimulation wire 14 is connected to nerve stimulator device NSD.

The resultant assembly is then placed in the patient by advancing epidural needle 12 into tissue until distal end 12A punctures nerve sheath NS and is beside nerve plexus NP, such as the brachial nerve plexus by bicep B of the patient. Next, a pulse voltage is supplied from nerve stimulator device NSD to determine the correct location of distal end 12A.

Also, after twisting proximal end 16B of multi-purpose connector 16 shut, syringe S may be employed to aspirate and to withdraw fluid, which visually indicates that the puncture has been successful and the correct body cavity has been located, i.e., distal end 12A should be lying within nerve sheath NS and proximate to nerve plexus NP, as opposed to puncturing into artery AR or vein VE or nerve plexus NP. Thus, if the aspirated fluid is blood, the person operating the assembly can determine that a blood vessel inadvertently has been punctured, and appropriately re-position the assembly. Syringe S is also employed to administer a solution, such as local anesthesia LA or saline, as described in more detail further below.

With reference now to FIG. 3, shown are the thumb and first finger of a person beginning to insert epidural catheter 20 into proximal end 16B of multi-purpose connector 16. Alternatively, beginning of insertion of epidural catheter 20 may be accomplished prior to advancing epidural needle 12 through tissue until its distal end 12A is located beside nerve plexus NP. Epidural catheter 20 may be provided with markers for checking the length of catheter insertion.

With reference now to FIG. 4, after the user has continued to push epidural catheter 20 through multi-purpose connector 16, and into and through epidural needle 12, eventually distal end 20A of epidural catheter 20 will protrude out of distal end 12A of epidural needle 12 and into and through nerve sheath NS and be lying alongside nerve plexus NP of the patient.

Epidural catheter 20 may suitably be an elongate, flexible plastic catheter hose (such as 20 gauge), the outer diameter of which is smaller than the inner diameter of each of epidural needle 12 and multi-purpose connector 16. Distal end 20A of epidural catheter 20 may suitably be radiopaque so that an additional way of determining proper location may be vis-a-vis x-ray. The drug for the regional anesthesia is injected through epidural catheter 20 by way of its proximal end 20B being connected to a syringe that is connected to a drug supply.

Previously to, concurrently with, or after supplying regional anesthesia by way of epidural catheter 20, a solution such as local anesthesia LA is optionally supplied from syringe S through tubing 18, into and through multi-purpose connector 16, and into and through epidural needle 12 and out needle distal end 12A. It is noted that if local anesthesia LA is going to be supplied through tubing 18 prior to insertion of epidural catheter 20, then, proximal end 16B of multi-purpose connector 16 is to be twisted shut so that the aperture at the terminus of distal end 16B used for insertion of epidural catheter 20 does not allow local anesthesia LA to leak back out of it. Hemostatic valve HV prevents back leakage of local anesthesia LA.

Figure 5:
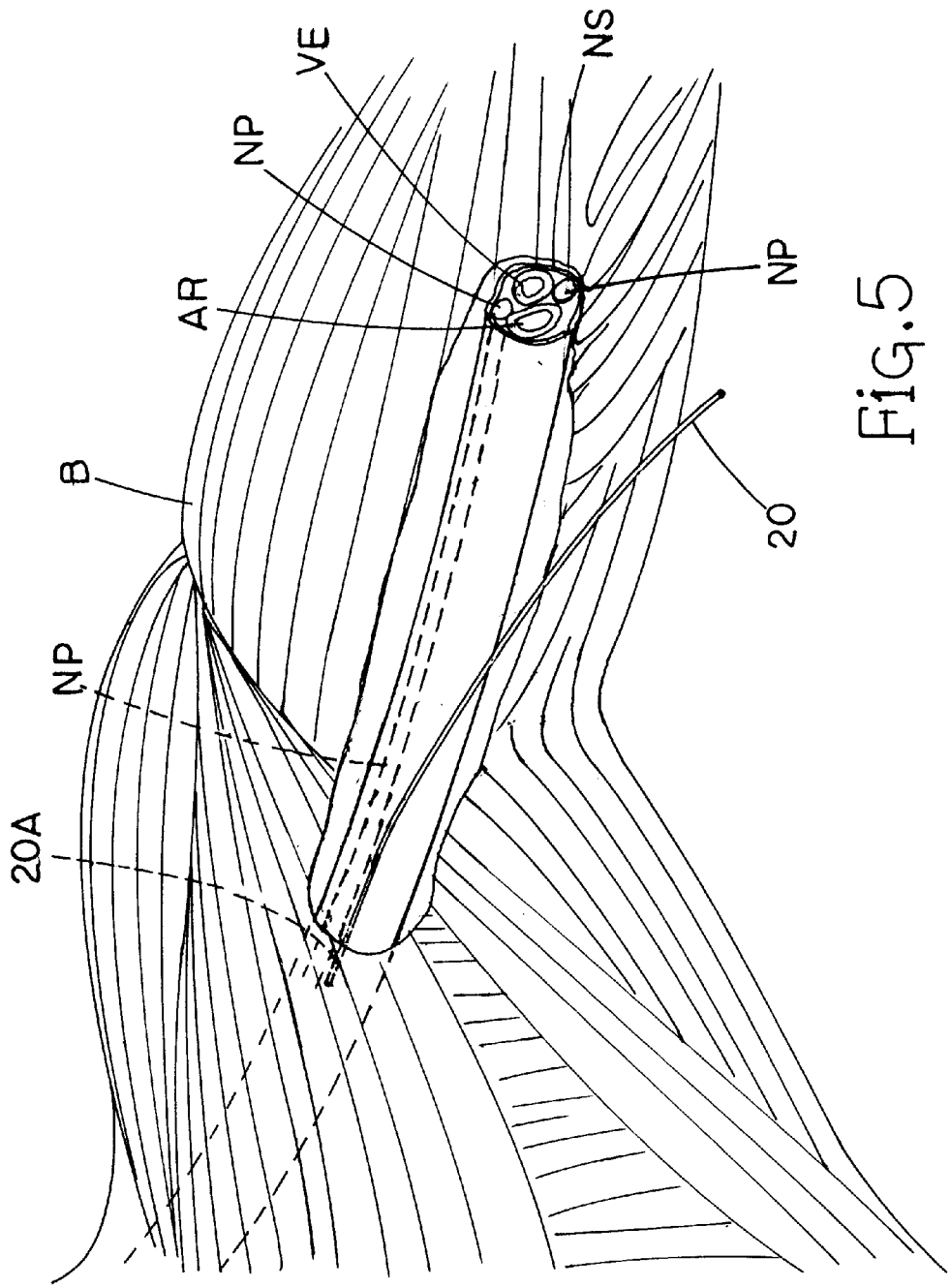
FIG. 5 is a view similar to FIG. 4, but further showing the epidural catheter left in place in the patient after removal of the epidural needle (and its associated stimulation wire) and the multi-purpose connector (and its associated tubing) of the catheter system.

Lastly, as can best be seen with reference to FIG. 5, epidural needle 12 (and its attached stimulation wire 14) and also multi-purpose connector 16 (and its attached tubing 18 with syringe S) are all slidably moved back by the person operating catheter system 10 and removed from epidural catheter 20, after having momentarily disconnected epidural catheter 20 from the syringe and supply of regional anesthesia. Thus, epidural catheter 20 is left in place, and re-attached to the syringe and supply of regional anesthesia. Even after the surgery is completed, epidural catheter 20 can be disconnected from the syringe and supply of regional anesthesia, and still left in place so that epidural catheter 20 may be employed further for administration of analgesic.

The method of use of catheter system 10 can also be similarly described in discrete steps 1–12 as set forth below.

1. Withdraw the stylet from the insulated TUOHY needle and attach the adapter assembly by rotating its spin-lock collar clockwise onto the needle hub. Orientation of the tubing (attached at its distal end to the adapter middle opening) can be adjusted by loosening the spin-lock collar, and adjusting the direction of the tubing and re-tightening the collar.
2. Attach the syringe filled with sodium chloride solution, neurolytic solution, or anesthetic solution to the proximal end of the tubing. Then, prime the tubing and the TUOHY needle with solution.
3. If a peripheral nerve stimulator device is used, attach its electrode pin to the conducting wire connected to the insulated TUOHY needle.
4. After raising a skin wheal with solution, introduce the TUOHY needle through the puncture site towards the targeted neurovascular bundle at an angle of about 30°. (Some physicians suggest an angle of 10–20°.)
5. Turn on the nerve stimulator device and advance the TUOHY needle in the direction of the nerve until visible muscle contractions occur in the innervated area.
6. Reduce the current from the nerve stimulator device and optimize the needle position until muscle contraction occurs at lower current levels. The tip of the needle has reached an optimal position, i.e., puncturing the nerve sheath and being located beside the nerve plexus, when noticeable contractions occur at a current of approximately 0.2 to 0.5 mA (higher current levels may be required for certain nerve blocks). Then, aspirate for possible intravascular placement.

7. Following negative aspiration, a test dose of a milliliter of local anesthetic can be injected through the tubing. Muscle contractions should cease within 2 to 10 seconds. Prior to in-dwelling catheter placement, the desired dose of anesthetic agent can be injected through the tubing.

8. The pink plastic threading assist guide should be removed from the in-dwelling catheter. The catheter should then be inserted through the hemostatic valve of the adapter, and then continued through the adapter and through the insulated TUOHY needle.

9. Insert the catheter to the desired depth, with the distal end of the catheter protruding out of the distal end of the needle (which is determined by the markings on the catheter), and hold the catheter in place and slowly remove the insulated TUOHY needle/adapter device.

10. Introduce the proximal end of the catheter as far as possible in the central opening of the transparent screw cap of the catheter connection (not shown) for administration of regional anesthesia.

11. Tighten screw cap firmly until the catheter can no longer be withdrawn (usually 2 or more rotations) from the connection to the regional anesthesia.

12. Finally, aspirate and administer additional regional anesthesia through the epidural catheter as needed.

It will be understood that various details of the invention may be changed without departing from the scope of the invention. Furthermore, the foregoing description is for the purpose of illustration only, and not for the purpose of limitation—the invention being defined by the following, appended claims.

What is claimed is:

1. A catheter system comprising:
   (a) an epidural needle, having a distal end and a proximal end, with the distal end terminating in an aperture and having a tip adapted for insertion through tissue into a nerve sheath of a patient, and with the proximal end being adapted for fluid connection;
   (b) an electrically conductive stimulation wire connected at one end of the stimulation wire to the epidural needle in a manner that allows for conduction of an electrical voltage along the stimulation wire to the distal end of the epidural needle and at another end of the stimulation wire being adapted for connection to a nerve stimulator device;
   (c) a multi-purpose connector adapted for administration of local anesthesia or the like, and having a distal end, a proximal end, and a middle aperture, with the distal end being adapted for fluid connection to the epidural needles's proximal end, and with the proximal end being adapted to selectively close the multi-purpose connector and to receive an epidural catheter, and with the middle aperture being adapted for fluid connection to flexible tubing; and
   (d) an epidural catheter adapted for administration of regional anesthesia or the like, and having a distal end terminating in an opening, and being adapted for insertion within and through the multi-purpose connector and further insertion within and through the epidural needle.

2. The catheter system of claim 1, wherein the epidural needle is provided with insulation substantially along the length thereof.

3. The catheter system of claim 1, wherein the epidural needle's proximal end includes a hub for fluid connection to the multi-purpose connector's distal end.

4. The catheter system of claim 3, wherein the epidural needle is a TUOHY needle, the epidural needle's hub for fluid connection is a TUOHY needle hub, and the epidural needle's tip is a HUBER tip.

5. The catheter system of claim 1, wherein the multi-purpose connector is an adapter, and the multi-purpose connector's distal end defines a hemostatic valve.

6. The catheter system of claim 1, further including flexible tubing that is an intravenous tube having a distal end and a proximal end, with the tube's distal end fluidly connected to the middle aperture of the multi-purpose connector and the tube's proximal end fluidly connected to a syringe for administration of local anesthesia.

7. A method for administration of regional anesthesia or the like to a patient, said method comprising the steps of:
   (a) providing (i) an epidural needle, having a distal end and a proximal end, with the distal end terminating in an aperture and having a tip adapted for insertion through tissue into a nerve sheath and proximate to a nerve plexus within the nerve sheath of a patient, and (ii) an electrically conductive stimulation wire connected at one end of the stimulation wire to the epidural needle in a manner that allows for conduction of an electrical voltage along the stimulation wire to the distal end of the epidural needle and at another end of the stimulation wire being adapted for connection to a nerve stimulator device;
   (b) fluidly connecting a multi-purpose connector, adapted for administration of local anesthesia or the like, and having a distal end, a proximal end, and a middle aperture, at the multi-purpose connector's distal end to the epidural needle's proximal end, and wherein the multi-purpose connector's proximal end is adapted to selectively close the multi-purpose connector and to receive an epidural catheter, and wherein the multi-purpose connector's middle aperture is adapted for fluid connection to flexible tubing;
   (c) inserting the epidural needle, having the wire and multi-purpose connector connected thereto, via the epidural needle's tip through the tissue and into the nerve sheath and proximate to the nerve plexus of the patient;
   (d) conducting an electrical voltage along the wire to determine correct positioning of the epidural needle's tip within the nerve sheath and proximate to the nerve plexus of the patient;
   (e) inserting an epidural catheter, adapted for administration of regional anesthesia or the like and having a distal end terminating in an opening, within and through the multi-purpose connector and within and through the epidural needle, in order to locate the epidural catheter within both the multi-purpose connector and the epidural needle, with the epidural catheter's distal end protruding out of the epidural needle's distal end within the nerve sheath and proximate to the nerve plexus of the patient;
   (f) administering regional anesthesia or the like via the epidural catheter; and
   (g) optionally administering local anesthesia or the like via the multi-purpose connector at any time after step (c).

8. The method of claim 7, wherein the epidural needle is provided with insulation substantially along the length thereof.

9. The method of claim 7, wherein the epidural needle's proximal end includes a hub for fluid connection to the multi-purpose connector's distal end.

10. The method of claim 9, wherein the epidural needle is a TUOHY needle, the epidural needle's hub for fluid connection is a TUOHY needle hub, and the epidural needle's tip is a HUBER tip.

11. The method of claim 7, wherein the multi-purpose connector is an adapter, and the multi-purpose connector's distal end defines a hemostatic valve.

12. The method of claim 7, further including fluidly connecting flexible tubing that is an intravenous tube, having a distal end and a proximal end, at the tube's distal end to the middle aperture of the multi-purpose connector, and fluidly connecting the tube's proximal end to a syringe for administration of local anesthesia.

13. The method of claim 7, further including prior to step (d), attaching a syringe to the middle opening of the multi-purpose connector and aspirating with the syringe to check aspirated fluid for blood therein to determine correct positioning of the epidural needle's tip within the nerve sheath and proximate to the nerve plexus.

14. The method of claim 7, further including removing the epidural needle and the multi-purpose connector from the epidural catheter, and leaving the epidural catheter in place in the patient.

* * * * *